US00PP08834P

United States Patent [19]

Van der Salm

[11] Patent Number: Plant 8,834

[45] Date of Patent: Jul. 12, 1994

[54] LILY PLANT: LILIUM 'PINK PARAMOUNT'

[76] Inventor: Gerardus C. Van der Salm, 35306 NW. Toenjes Rd., Woodland, Wash. 98674

[21] Appl. No.: 111,641

[22] Filed: Aug. 24, 1993

[51] Int. Cl.[5] ..... A01H 5/00

[52] U.S. Cl. ..... Plt./87.4

[58] Field of Search ..... Plt. 87.4

*Primary Examiner*—David T. Fox

[57] ABSTRACT

A new variety of hybrid lily plant bearing large upfacing flowers of excellent form and long persistence, both on the plant and as cut-flowers. The flowers of the new plant are particularly characterized by their medium pink coloration, their white-edged green nectaries, their deeply colored papillae, their lightly ruffled margins, their large size and substance, their completely upfacing orientation, and the upwardly curving pedicels of the lower flowers. This combination is completely new in the Oriental hybrid divisions of lilies suited to forcing and to mass commercial cultivation. The variety is highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in Woodland, Wa., in 1987. The breeding efforts had as their objective the production of large-flowered completely upfacing Oriental hybrids in a variety of shades of pink, with deeply pigmented papillae, suited to forcing into flower out of season, heretofore unknown in the lily breeding art.

I achieved the desired objective by intercrossing unnamed upright and semi-upright Oriental seedlings which carried pink flower color and were also suited to forcing for yearround use as cut-flowers.

The unnamed Oriental seedlings which were the parents of 'Pink Paramount' were produced by me, from a series of crosses among seedlings which were selected in my fields from large seedling populations of my own crosses. The original crosses came from material unique to my own breeding lines and not available in the trade. the field-selected seedlings were genetically very diverse, and 100 seedlings were selected from their outstanding vigor, stem length, pink flower color, and upfacing or semi-upfacing flower orientation. These were forced into flower under glass, and the 25 seedlings which showed the best forcing performance were then randomly intercrossed to produce a large quantity of seed. This seed was grown to flowering size, producing a large population of seedlings, from which the best 100 were again selected for vigor, stem length, pink flower color, and upfacing or semi-upfacing flower orientation. These were subsequently tested for their forcing performacne, and 'Pink Paramount' was selected as one of the seedlings best suited for forcing as a cut-flower.

The flowers of my new lily are characterized by a completely upfacing orientation, large size, unusually thick substance, lightly ruffled tepal margins, and a distinctive medium pink coloration accented by white-edged green nectaries and by deep pink papillae, a combination unique among Oriental hybrid lilies. The pedicels of the lower flowers emerge from the stem at an angle only slightly ascending, with a sharp upward curve about 5 to 8 cm from the base of each pedicel. These uniquely curved pedicels minimize the breaking off of the buds during their handling as cut-flowers. The variety possesses unusally strong, stout stems. In addition, the clone possesses to a high degree desirable characteristics of hybrid vigor. The clone is a good grower and propagator, as observed at Woodland, Wa.

My new variety of lily plant has been asexually reproduced by me and under my direction at Woodland, Wa. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive completely upfacing medium pink flowers with lightly ruffled tepal margins, white-edged green nectaries, and deep pink papillae, and also the unique curvature of the pedicels of the lower buds and the ascending pedicels of the upper buds, which minimize bud breakage during handling of the cut-flowers.

DESCRIPTION OF THE NEW VARIETY

The following is a detailed description of my new variety of Oriental hybrid lily, with nomenclature according to the *International Lily Register* (The Royal Horticultural Society of London, Second Edition, 1969), and with color designations according to the Colour Chart of The Royal Horticultural Society, published by the Society in 1966.

The Plant

Origin: Seedling.

*Seed parent.*—Selected unnamed Oriental hybrid seedling.

*Pollen parent.*—Selected unnamed Oriental hybrid seedling.

Commercial classification: Hybrid Lilium clone.

Horticultural classification: Division VII-B, bowl-shaped Oriental hybrid lily, according to the Horticultural Classification of Lilies, Royal Horticultural Society of London.

Form: Single stem, erect and stately.

Heights: 80 to 125 cm from bulbs 14 to 18 cm in circumference, provided their light levels are adequate; low light levels may cause "stretching."

Growth: Vigorous and upright.

Foliage quantity: Abundant.

Size of leaf: Broad, 4 to 7 cm wide × 10 to 14 cm long.

Shape of leaf: Lanceolate (pointed).

Texture: Leathery and glossy.

Color: Medium green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 12 to 16 cm long and 10 to 14 cm in circumfreence just prior to opening.

Opening: Bud opens slowly, in response to morning light; this takes about one about hour.

Color: Soft Pink (R.H.S. Colour Chart red-purple 68 C/D), with very soft green to white midribs.

Peduncle: Averages 4 to 6 cm, but it may elongate if light levels are too low or if bulbs have been improperly stored prior to forcing. Color is medium green with very light plum overlay.

The Flower

Blooming habit: Annually in midseason; flowers once and profusely.

Size: Flowers are large-sized, averaging 20 to 28 cm in diameter, reflexing at the tips on the second day to 18 to 22 cm in diameter. The tepals are broad: outer tepals are 3 to 4 cm wide, and inner tepals are 4.75 to 6 cm wide.

Borne: In a single racemic inflorescence producing 4 to 8 flowers from a bulb 14 to 16 cm in circumfrence.

Shape: Form a broad bowl shape by the second day after opening, with the "bowl" 5 to 6 cm deep.

Tepalage: Typical of genus Lilium, with 6 imbricated tepals.

Tepal color: R.H.S. Colour Chart red-purple 66 C to 68 C/D, shading to 68 B along the midrib and at the tepal tips, depending upon growing tempertures and light levels. A white margin 2 to 10 mm wide borders the light green nectaries. The pink color may it decrease with high temperatures and low light levels, and it may deepen slightly with cool temperatures and high light levels.

Tepal spotting: The basal half of each tepal is spotted with deep magenta rose (R.H.S. Colour Chart red-purple 59 B -60 B) papillae of moderate size. Papillae immediately adjacent to the nectaries are extremely elongated and are not pigmented.

Tepal longevity: Tepals on stems about three weeks.

Pedicel length: Average 8 to 12 cm long.

Pedicel color: Medium green very light plum overlay.

Pedicel form: Sturdy, flexible, and ascending, with lower pedicels only slightly ascending at the base, but curving sharply upward at a point 5 to 8 cm from the base.

Color changes: Flowers become slightly lighter and a more lavender-toned pink as the flowers age. Low light levels and extreme heat may cause the pink pigmentation to decrease Appearance: Flower is shiny.

Disease resistance: The flower and plant are resistant to disease; in particular, they are resistant to Fusarium bulb rot and Botrytis blight.

Fragrance: Light sweet fragrance.

Lasting quality: The flower is long lasting, both on the plant and as a cut-flower.

The Reproductive Organs

Stamens: Arrangement typical of genus Lilium. Six stamens with soft green to white filaments 8 to 10 cm long.

Pollen and anthers (dehisced): R.H.S. Colour Chart greyed red 180 A to greyed purple 183 A.

Pistil: One in number, 10 to 12 cm long.

Stigma: Soft puple R.H.S. Colour Chart 186 C/D, large in size.

Characteristics of ovary: Characteristic of genus Lilium.

The Fruit

Fertility: The fruit bears fertile seed.

Shape: Ovoid.

Color at maturity: Soft brown, sometimes overlaid with soft plum.

My new variety of Oriental hybrid lily most nearly resembles 'Joy,' but it has much larger and thicker flowers with much longer tepals, a deeper pink color, deeply colored papillae, and a white margin bordering the green nectaries. The flowers are completely upfacing, the pedicels are completely ascending, and the lower pedicels show a sharp upward curvature at a point 5 to 8 cm from the base of the pedicel.

I claim:

1. A new and distinctive variety of Oriental hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in particular by its unique completely upfacing flowers with lower pedicels curving sharply upward at a point 5 to 8 cm from the base of the pedicel, and by its medium pink coloration with white-edged green nectaries and with very deep magenta rose papillae on the basal half of each tepal, a combination unique amont Oriental hybrid lilies suited to forcing and to mass commercial cultivation.

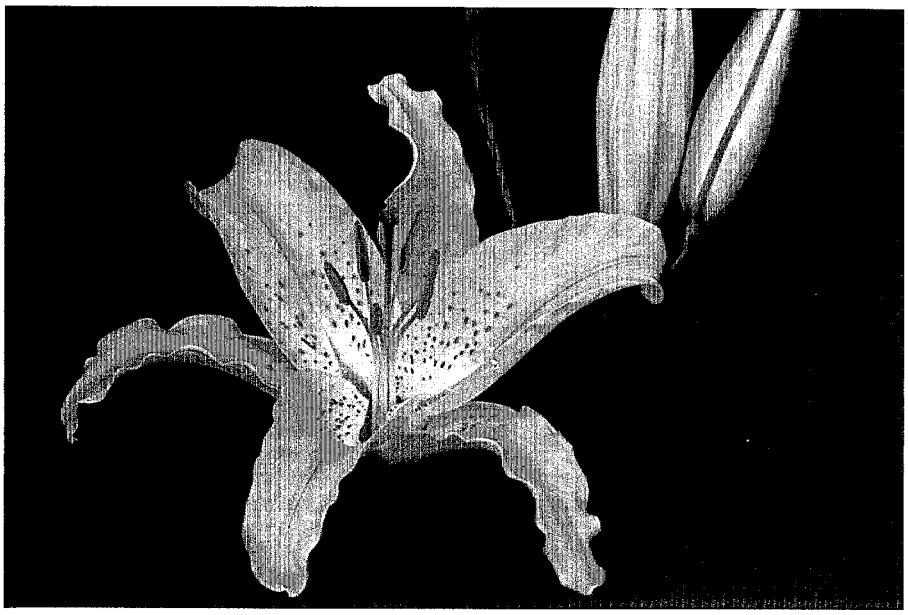

* * * * *